(12) United States Patent
Yu et al.

(10) Patent No.: US 8,883,137 B2
(45) Date of Patent: Nov. 11, 2014

(54) COMPOSITIONS COMPRISING SELENIUM-RICH YEAST AND YEAST BETA-GLUCAN

(75) Inventors: Xuefeng Yu, Yichang (CN); Zhihong Li, Yichang (CN); Minghua Yu, Yichang (CN); Juan Yao, Yichang (CN); Yan Zhang, Yichang (CN); Yamin Zhu, Yichang (CN)

(73) Assignee: Angel Yeast Co., Ltd., Yichang (CN)

( * ) Notice: Subject to any disclaimer, the term of this patent is extended or adjusted under 35 U.S.C. 154(b) by 1471 days.

(21) Appl. No.: 12/264,331

(22) Filed: Nov. 4, 2008

(65) Prior Publication Data

US 2009/0269322 A1    Oct. 29, 2009

(30) Foreign Application Priority Data

Apr. 29, 2008 (CN) .......................... 2008 1 0105513

(51) Int. Cl.
| | |
|---|---|
| *A61K 38/44* | (2006.01) |
| *A01N 59/02* | (2006.01) |
| *A61K 36/06* | (2006.01) |
| *A23L 1/303* | (2006.01) |
| *A23L 1/30* | (2006.01) |
| *A23L 1/302* | (2006.01) |
| *A23L 1/304* | (2006.01) |

(52) U.S. Cl.
CPC ............... *A23L 1/3016* (2013.01); *A61K 36/06* (2013.01); *A23L 1/3002* (2013.01); *A23L 1/302* (2013.01); *A23L 1/304* (2013.01)
USPC .......... 424/93.51; 424/94.4; 424/94.1; 426/62

(58) Field of Classification Search
None
See application file for complete search history.

(56) References Cited

U.S. PATENT DOCUMENTS

| 5,904,924 | A * | 5/1999 | Gaynor et al. | ............ 424/195.17 |
|---|---|---|---|---|
| 6,451,341 | B1 * | 9/2002 | Slaga et al. | .................... 424/468 |
| 2003/0159702 | A1 * | 8/2003 | Lindell et al. | ................. 131/270 |

OTHER PUBLICATIONS

Eva S. Wintergerst, Silvia Maggini, & Dietrich H. Hornig "Contribution of Selected Vitamins and Trace Elements to Immune Function" Annals of Nutrition & Metabolism, Aug. 28, 2007, 51(4), pp. 301-323.*
Kirkey, Sharon "Surgeon Believes Antioxidants will Cure 'Incurable' Diseases: Diet, Supplements Can Slow 'Rotting' of Aging Bodies" [Final Edition] The Ottawa Citizen, Oct. 7, 1998, p. D6 (2 pages).*
Grigorij Kogan, Andrej Staško, KatarIna Bauerová, Martin Polovka, Ladislav Šoltés, Vlasta Brezová, Jana Navarová, Danica Mihalová "Antioxidant Properties of Yeast (1→3)β-d-Glucan Studied by Electron Paramagnetic Resonance Spectroscopy and Its Activity in the Adjuvant Arthritis" Carbohydrate Polymers, 61(1), Jul. 4, 2005, pp. 18-28.*
Chong, E W-T; Wong, T Y; Kreis, A J; Simpson, J A; and Guymer, R H "Dietary Antioxidants and Primary Prevention of Age Related Macular Degeneration: Systematic Review and Meta-analysis" BMJ, 2007 (published Oct. 11, 2007), 335 p. 755-762.*
Kaur "Selenium enrichment and anti-oxidant status in baker's yeast, *Saccharomyces cerevisiae* at different sodium selenite concentrations" Nutr Hosp. 2006,21 (6), pp. 704-708.*
Davis, K "Optimizing Your Diet: Best Foods for Specific Vitamins", MIT Sports Medicine, <URL:http://web.mitedu/athletics/sportsmedicine/wcrvitamins.html>, accessed Jan. 23, 2012, archived Nov. 7, 2006, 13 pages.*
Tylee, P. et al "Vitamin B1-Thiamine" Healthy Vitamin Choice, <URL:http://www.healthy-vitamin-choice.com/vitamin-b1.htm>, accessed Jan. 23, 2013, archived Aug. 10, 2007, 3 pages.*
Tallarida, R.J., "Combinations of Chemicals" and "Calculations for Combination Drug Analysis", Drug Synergism and Dose-Effect Analysis, Chapman & Hall/CRC, 2000, chapters 1 and 4, pp. 1-13 and 57-71.*

* cited by examiner

*Primary Examiner* — Jon P Weber
*Assistant Examiner* — Aaron J Kosar
(74) *Attorney, Agent, or Firm* — Matthias Scholl P.C.; Matthias Scholl

(57) ABSTRACT

A nutritional composition comprising by weight: between 0.05 and 30% selenium-enriched yeast; between 1 and 90% yeast beta-glucan; between 0.5 and 60% Vitamin C; and between 0.5 and 40% Vitamin E. The composition features anti-oxidative, anti-aging, cancer-preventing, and immune-stimulating properties.

16 Claims, No Drawings

COMPOSITIONS COMPRISING SELENIUM-RICH YEAST AND YEAST BETA-GLUCAN

CROSS-REFERENCE TO RELATED APPLICATIONS

This application claims priority benefits to Chinese Patent Application No. 200810105513.3 filed on Apr. 29, 2008, the contents of which are incorporated herein by reference.

BACKGROUND OF THE INVENTION

1. Field of the Invention

The invention relates to a health-promoting composition, and more particularly to a health promoting composition comprising selenium-rich yeast and yeast beta-glucan.

2. Description of the Related Art

Although it is toxic in large doses, selenium is an essential micronutrient for animals. Dietary selenium comes from nuts, cereals, meat, fish, and eggs. Brazil nuts are the richest ordinary dietary source (though this is soil-dependent, since the Brazil nut does not require high levels of the element for its own needs). High levels are found in kidney, tuna, crab, and lobster, in that order. In general, however, the content of selenium in human diet is limited and insufficient.

In humans, selenium is a trace element nutrient which functions as cofactor for reduction of antioxidant enzymes such as glutathione peroxidases and certain forms of thioredoxin reductase found in animals and some plants (this enzyme occurs in all living organisms, but not all forms of it in plants require selenium).

Glutathione peroxidase (GSH-Px) catalyzes certain reactions which remove reactive oxygen species such as peroxide:

$$2GSH + H_2O_2 \text{-} GSH\text{-}Px \rightarrow GSSG + 2H_2O$$

Selenium also plays a role in the functioning of the thyroid gland by participating as a cofactor for the three known thyroid hormone deiodinases.

Selenium is a component of the unusual amino acids selenocysteine, and selenomethionine, and the amino acid dimer selenocystine, and as such is an important building block of the human body.

Furthermore, selenium is an important component in enzymes affecting metabolism, reproduction, immune system as well as the well being of human beings. It is also known to play a role in preventing cancer, anti-oxidation, and anti-aging.

Since there is insufficient amount of selenium present in normal diet, it is advantageous to supply selenium as food supplement. Inorganic selenium in the form of selenite, or organic selenium, for example, in the form of selenium-rich yeast may be supplied. However, there is a remarkable difference between inorganic selenium and organic selenium in terms of absorption and toxicity, i.e., inorganic selenium is much harder to absorb and has a much higher toxicity. Therefore, a commonly-used source of organic selenium is selenium-enriched yeast.

Using modern biotechnology, selenium-enriched yeast can be made by converting inorganic selenium into organic selenium using brewer's yeast and then separating and refining the organic selenium. 99% or more of all selenium in selenium-enriched yeast is in form of organic selenium, which facilitates faster absorption and low toxicity.

Yeast beta-glucan is a water-insoluble polysaccharide having β-1, 3-D-glucan as main chains and β-1, 6-D-glucan as side chains. It is an important component of yeast cell wall. It can improve immunity, prevent cancer, inhibit bacteria and reinforce resistance against illnesses.

In recent years, there have been many studies on selenium, majority of them focusing on the nutritional mechanism, and a large amount of products have appeared. However, there have been few products made from organic selenium or selenium-rich yeast. Specifically, rather than taking the comprehensive nutritional factor is into account, products have appeared with the sole goal of supplying selenium. In addition, researchers on yeast beta-glucan mainly concentrate on extraction and purification of beta-glucan, and few products, if any, exist.

SUMMARY OF THE INVENTION

Therefore, it is one objective of the invention to provide a composition comprising selenium-rich yeast and yeast beta-glucan exhibiting anti-oxidative, anti-aging, cancer preventive and immune-enhancing properties.

To achieve the above objectives, in accordance with one embodiment of the invention, provided is a nutritional composition comprising by weight: between 0.05 and 30% organic selenium-enriched yeast; between 1 and 90% purified yeast beta-glucan; between 0.5 and 60% Vitamin C; and between 0.5 and 40% Vitamin E.

In certain classes of this embodiment, the composition comprises by weight: between 0.5 and 10% selenium-enriched yeast; between 20 and 58% yeast beta-glucan; between 20 and 40% Vitamin C; and between 20 and 30% Vitamin E.

In certain classes of this embodiment, the selenium-enriched yeast comprises between 500 and 2000 ppm of selenium.

In certain classes of this embodiment, the yeast beta-glucan comprises by weight between 20 and 90% of beta-glucan.

In certain classes of this embodiment, the composition further comprises by weight: between 0 and 1% Vitamin A; between 0 and 5% β-carotene; between 0 and 1% Vitamin $B_1$; between 0 and 1% Vitamin $B_2$; between 0 and 1% Vitamin $B_6$; between 0 and 5% lycopene; between 0 and 20% grape seed extract; between 0 and 20% α-lipoic acid; between 0 and 20% propolis; between 0 and 10% ginkgo biloba extract; between 0 and 10% ginseng extract; between 0 and 30% calcium carbonate; between 0 and 30% calcium gluconate; between 0 and 30% calcium lactate; between 0 and 10% zinc gluconate; between 0 and 10% zinc lactate; between 0 and 10% ferrous gluconate fumarate; between 0 and 1% ferrous lactate; and between 0 and 10% ferrous fumarate.

The composition according of the invention can be formulated in the form of granules, powder, capsules, tablets, or liquid by adding auxiliary materials. The auxiliary materials are without limitation starch, milk powder, dextrin, microcrystalline cellulose, hydroxypropyl sodium cellulose, sugar, food flavoring, and so on.

Advantages of the Invention Include 1) the invention employs safe and highly-effective organic selenium-enriched yeast as the main selenium source, and the selenium content in the composition is between 10 and 1000 μg/g, which ensures its safety and health effects; and
2) high-purity yeast beta-glucan and natural Vitamin C and E are included in the composition to facilitate the synergistic effect, and to obtain a composition enriched in organic selenium and yeast beta-glucan promoting enhanced immunity and resistance to illness.

DETAILED DESCRIPTION OF THE EMBODIMENTS

Definitions:

The term "selenium-enriched yeast," as used herein, refers to dried, pulverized cells of Saccharomyces cerevisiae which have incorporated selenium into organic compounds. Selenium-enriched yeast used herein was purchased from Angel Yeast Co., Ltd. (Add: 24 Zhongnan Rd. Yichang Hubei 443003, China, Tel: 0086-717-6369254) under the commercial name of Selenium-enriched Yeast (selenium content of 2000 ppm). Selenium-enriched yeast used herein was prepared as follows: yeast (*Saccharomyces cerevisiae*) was cultured in a culture medium with enriched sodium selenite, subsequently the yeast was harvested, centrifugated and dried.

The term "yeast beta-glucan," as used herein, refers to polysaccharide chains of D-glucose molecules, with the six-sided D-glucose rings connected at the 1 and 3 positions, wherein side chains 1, 6-glucan side-chains branch off from the longer beta-1, 3 glucan backbone, produced by yeast. Yeast beta-glucan used herein was purchased from Angel Yeast Co., Ltd. (Add: 24 Zhongnan Rd. Yichang Hubei 443003, China, Tel: 0086-717-6369254) under the commercial name of 80% Yeast Glucan. Yeast beta-glucan used herein was prepared as follows: yeast was autolysed and centrifugated, and then yeast cell wall was collected, from which yeast glucan was extracted using base and acid.

Vitamin C was purchased from CSPC Weisheng Pharmaceutical (Shijiazhuang) Co., Ltd. (Add: No. 236 Yellow Rd., Shijiazhuang New-high Technology Industry Development Zone, Hebei, China, Tel: 0086-311-85388577) under the commercial name of 99% Coated Ascorbic Acid.

Vitamin E was purchased from BASF Vitamin Co., Ltd. (Add: No. 88 Yunhai Rd., Shenyang Economy and Technology Development Zone, Shenyang, China, Tel: 0086-24-25360235) under the commercial name of 50% Vitamin E.

β-carotene was purchased from BASF Vitamin Co., Ltd. (Add: No. 88 Yunhai Rd., Shenyang Economy and Technology Development Zone, Shenyang, China, Tel: 0086-24-25360235) under the commercial name of 10% β-carotene.

Vitamin $B_1$ was purchased from Guangzhou Topvita Food Ingredients Co., Ltd. (Tel: 0086-20-38390003) under the commercial name of 99% Thiamine hydrochloride.

Vitamin $B_2$ was purchased from Guangzhou Topvita Food Ingredients Co., Ltd. (Tel: 0086-20-38390003) under the commercial name of 99% Riboflavin.

Vitamin $B_6$ was purchased from Guangzhou Topvita Food Ingredients Co., Ltd. (Tel: 0086-20-38390003) under the commercial name of 99% Pyriddoxine.

Lycopene was purchased from Guangzhou Topvita Food Ingredients Co., Ltd. (Tel: 0086-20-38390003) under the commercial name of 6% Lycopene.

The term "grape seed extract," as used herein, refers to industrial derivatives from whole grape seeds comprising polyphenols, including oligomeric proanthocyanidins recognized as antioxidants. The grape seed extracts used herein was purchased from Ningbo Osaki Biotech Co., Ltd. (Add: No. 521 Yuanbaoshan Rd. Beilun Ningbo China, Tel: 0086-574-86119676) under the commercial name of Grape Seed Extract, with 95% Proanthocyanidins.

α-Lipoic acid was purchased from Tianjin Tiancheng Pharmaceutical Co., Ltd. (Add: P.O. BOX 4005 North Sanjing Rd. Yangliuqing Xiqing District, Tianjin, China, Tel: 0086-22-27390520) under the commercial name of 99% α-Lipoic acid.

The term "propolis," as used herein, refers to a resinous mixture that bees collect from tree buds, sap flows, or other botanical sources. Propolis used herein was purchased from Henan Purui Bees Products Co., Ltd. (Add: Dazhou Industrial zone, Changge, Henan, 461507, China, Tel: 0086-374-6865389) under the commercial name of 30-90% Propolis Powder.

The term "ginkgo biloba extract," as used herein, refers to an extract from Gingko biloba, a unique species of tree cultivated in China, Korea, and parts of Japan with no close living relatives, comprising flavonoid glycosides and terpenoids (ginkgolides, bilobalides). The ginkgo biloba extract used herein was purchased from Ningbo Osaki Biotech Co., Ltd. (Add: No. 521 YuanBaoshan Rd. Beilun Ningbo China, Tel: 0086-574-86119676) under the commercial name of Ginkgo Biloba Leaf Extract, with total Ginkgo flavone glycoside more than 24%.

The term "ginseng extract," as used herein, refers to an extract from Panax ginseng (white ginseng). The ginseng extract used herein was purchased from Ningbo Osaki Biotech Co., Ltd. (Add: No. 521 YuanBaoshan Rd. Beilun Ningbo China. Tel: 0086-574-86119676) under the commercial name of Panax Ginseng Root Extract, with 20% Ginsenosides.

Calcium carbonate was purchased from ZhengZhou RuiPu Biology Engineering Co., Ltd. (Add: No. 96 Ruida Rd. Hi-Tech Industries Development Zone ZhengZhou China. Tel: 0086-371-67896828) under the commercial name of Calcium carbonate with concentration no less than 96%.

Calcium gluconate was purchased from ZhengZhou RuiPu Biology Engineering Co., Ltd. (Add: No. 96 Ruida Rd. Hi-Tech Industries Development Zone ZhengZhou China. Tel: 0086-371-67896828) under the commercial name of Calcium gluconate with concentration no less than 99%.

Calcium lactate was purchased from ZhengZhou RuiPu Biology Engineering Co., Ltd. (Add: No. 96 Ruida Rd. Hi-Tech Industries Development Zone ZhengZhou China. Tel: 0086-371-67896828) under the commercial name of Calcium lactate with concentration no less than 98%.

Zinc gluconate was purchased from ZhengZhou RuiPu Biology Engineering Co., Ltd. (Add: No. 96 Ruida Rd. Hi-Tech Industries Development Zone ZhengZhou China. Tel: 0086-371-67896828) under the commercial name of Zinc gluconate with concentration no less than 97%.

Zinc lactate was purchased from ZhengZhou RuiPu Biology Engineering Co., Ltd. (Add: No. 96 Ruida Rd. Hi-Tech Industries Development Zone ZhengZhou China. Tel: 0086-371-67896828) under the commercial name of Zinc lactate with concentration no less than 98%.

Ferrous gluconate fumarate was purchased from ZhengZhou RuiPu Biology Engineering Co., Ltd. (Add: No. 96 Ruida Rd. Hi-Tech Industries Development Zone, ZhengZhou, China. Tel: 0086-371-67896828) under the commercial name of Ferrous gluconate with concentration no less than 95%.

Ferrous lactate was purchased from ZhengZhou RuiPu Biology Engineering Co., Ltd. (Add: No. 96 Ruida Rd. Hi-Tech Industries Development Zone, ZhengZhou, China. Tel: 0086-371-67896828) under the commercial name of Ferrous lactate with concentration no less than 98%.

Ferrous fumarate was purchased from ZhengZhou RuiPu Biology Engineering Co., Ltd. (Add: No. 96 Ruida Rd. Hi-Tech Industries Development Zone, ZhengZhou China. Tel: 0086-371-67896828) under the commercial name of Ferrous fumarate with concentration no less than 93%.

The following embodiments are solely intended to describe the invention, not to limit the scope of the invention.

EXAMPLE 1

The nutritional composition of this example comprises by weight: 10% selenium-enriched yeast (selenium content of 2000 ppm), 30% yeast beta-glucan (beta-glucan content of 80% by weight), 20% Vitamin E, and 40% Vitamin C.

The preparation process comprises the following steps:
a) grinding: grinding Vitamin C and Vitamin E with a superfine pulverizer before mixing;
b) sieving: passing the grinded Vitamin C and Vitamin E through a 60 mesh sieve, and passing the selenium-enriched yeast and the yeast beta-glucan through a 60 mesh sieve;
c) mixing: manually mixing sieved selenium-enriched yeast with Vitamin E; placing the mixture into a mixer; placing the sieved beta-glucan and the grinded Vitamin C into V-shaped mixer to mix for 45 minutes. The mixer can be any type of mixer known in the art;
d) formulating: formulating the mixture into capsules, 1 g material for each capsule;
e) packing: packing 200 capsules into a bottle.

To ensure safety of products, all of the above steps are completed in a GMP facility.

EXAMPLE 2

The preparation process is substantially the same as that in example 1, with the only difference being that the nutritional composition comprises by weight: 30% selenium-enriched yeast (selenium content of 1000 ppm), 69% yeast beta-glucan (beta-glucan content of 70%), 0.5% Vitamin E, and 0.5% Vitamin C.

EXAMPLE 3

The preparation process is substantially the same as that in example 1, with the only difference being that the nutritional composition comprises by weight: 0.05% selenium-enriched yeast (selenium content of 500 ppm), 90% yeast beta-glucan (beta-glucan content of 90%), 6.95% Vitamin E, and 3% Vitamin C.

EXAMPLE 4

The nutritional composition of this example comprises by weight: 5% selenium-enriched yeast (selenium content of 1000 ppm), 30% yeast beta-glucan (beta-glucan content of 80%), 20% Vitamin E, 30% Vitamin C, and 15% sucrose.

The preparation process comprises the following steps:
a) grinding: grinding sucrose, Vitamin C and Vitamin E with a superfine pulverizer before mixing;
b) sieving: passing the grinded sucrose, Vitamin C and Vitamin E through a 60 mesh sieve, and passing the selenium-enriched yeast and the yeast beta-glucan through a 60 mesh sieve;
c) mixing: mixing sieved sucrose, Vitamin C, Vitamin E, selenium-enriched yeast, and yeast beta-glucan with sterile water in the proportion of 1:10 (n/v, g/mL) to form a liquid for oral administration;
d) packing: canning the oral liquid into bottles, 100 mL to each bottle.

To ensure safety of products, all of the above steps are completed in a GMP facility.

EXAMPLE 5

The nutritional composition of this example comprises by weight: 10% selenium-enriched yeast (selenium content of 1500 ppm), 40% yeast beta-glucan (beta-glucan content of 90%), 10% Vitamin E, 10% Vitamin C, 5% β-carotene, 5% lycopene, 5% propolis, 5% starch, and 10% sucrose.

The preparation process comprises the following steps:
a) grinding: grinding Vitamin C and Vitamin E with a superfine pulverizer before mixing;
b) sieving: passing the grinded Vitamin C and Vitamin E through a 60 mesh sieve, and passing the selenium-enriched yeast and the yeast beta-glucan through a 60 mesh sieve;
c) mixing: manually mixing sieved selenium-enriched yeast with Vitamin E; placing the mixture into a V-shaped; adding sieved beta-glucan and grinded Vitamin C and mixing for 45 minutes;
d) formulating: formulating the mixed materials into tablets, each tablet being 1.0 g; and
e) packing: packing into bottles or aluminum foil.

To ensure safety of products, all of the above steps are completed in a GMP facility.

EXAMPLE 6

The nutritional composition of this example comprises by weight: 17% selenium-enriched yeast (selenium content of 2000 ppm), 30% yeast beta-glucan (beta-glucan content of 80%), 10% calcium carbonate, 10% propolis, 5% Vitamin E, 5% β-carotene, 5% ginkgo biloba extract, 5% grape seed extract, 5% Vitamin C, 0.5% Vitamin $B_1$, 0.5% Vitamin $B_2$, 0.5% Vitamin $B_6$, 1% ferrous lactate, and 0.5% zinc gluconate.

The preparation process comprises the following steps:
a) grinding: grinding Vitamin C and Vitamin E in a superfine pulverizer before mixing;
b) sieving: passing the grinded Vitamin C and Vitamin E through a 60 mesh sieve, and passing the selenium-enriched yeast and the yeast beta-glucan through a 60 mesh sieve;
c) mixing: manually mixing sieved selenium-enriched yeast with Vitamin E, placing in a V-shaped mixer; adding sieved yeast beta-glucan and grinded Vitamin C into the mixer and mixing for 45 minutes;
d) formulating: placing the mixture into capsules, 1 g material for each capsule;
e) packing: packing capsules into bottles, 100 capsules per bottle.

To ensure safety of products, all of the above steps are completed in a GMP facility.

EXAMPLE 7

The preparation process is substantially the same as that in example 6, with the only difference being that the nutritional composition comprises by weight: 0.5% selenium-enriched yeast (selenium content of 1000 ppm), 58% yeast beta-glucan (beta-glucan content of 90%), 4.5% Vitamin E, 20% Vitamin C, 1% Vitamin A, 5% α-lipoic acid, 4% ginseng extract, 2% calcium carbonate, 1% zinc lactate, and 4% ferrous gluconate.

EXAMPLE 8

The preparation process is substantially the same as that in example 6, with the only difference being that the nutritional composition comprises by weight: 1% selenium enriched yeast (selenium content of 1500 ppm), 20% yeast beta-glucan (beta-glucan content of 60%), 30% Vitamin E, 15% Vitamin C, 0.5% Vitamin A, 1% Vitamin $B_1$, 1% Vitamin $B_2$, 1%

Vitamin $B_6$, 20% grape seed extract, 2% calcium lactate, 2.5% ferrous fumarate, and 5% dextrin.

EXAMPLE 9

Immunity Experiment on Composition 60 male BALB/c mice of clean grade with body weight 18-22 g were purchased from Shanghai Xipu'er-Bikai Experimental Animal Co., Ltd. (Add: No. 779 Laohumin Rd., Shanghai 200237, China, Tel: 0086-21-64776624) and randomly assigned into an experimental group, four control groups and a blank group with 10 animals in each group.

0.50 g/kg·bw of the nutritional composition of the Example 1 were administered to the experimental group by gavage daily. 0.05 g/kg·bw of selenium-enriched yeast (control group 1), 0.15 g/kg·bw of yeast beta-glucan (control group 2), 0.20 g/kg·bw of Vitamin C (control group 3) and 0.10 g/kg·bw of Vitamin E (control group 4) were administered to the four control groups respectively. Physiological saline was administered to the blank group.

Three months later, a plurality of immune index of mice comprising thymus weight/body weight ratio, humoral immunity function (antibody index) and cellular immune function (NK cell activity) were measured. The measurement method was the same as the method for evaluating health food.

| Groups | Animal quantity | Thymus weight/body weight ratio (mg/g) | Antibody cell detection Quantity of plaque forming cells (/106 spleen cells) | NK cell activity (%) |
|---|---|---|---|---|
| Blank group | 10 | 1.83 ± 0.44 | 93 ± 30 | 17.69 ± 5.62 |
| Control group 1 | 10 | 1.73 ± 0.25 | 92 ± 27 | 14.89 ± 7.92 |
| Control group 2 | 10 | 1.84 ± 0.61 | 92 ± 34 | 17.62 ± 9.91 |
| Control group 3 | 10 | 1.80 ± 0.57 | 87 ± 41 | 18.18 ± 4.14 |
| Control group 4 | 10 | 1.90 ± 0.33 | 96 ± 21 | 18.02 ± 5.31 |
| Experimental group | 10 | 2.87 ± 0.48* | 184 ± 41** | 32.99 ± 10.08** |

Remark:
Symbol "*" represents $p < 0.05$ by comparison with the blank group;
symbol "**" represents $p < 0.01$ by comparison with the blank group.

From the experimental results, a conclusion can be drawn that compared with the blank group and four control groups, the nutritional composition of the Example 1 can enhance the immunity and improve the antibody producing capacity and NK cell activity of the mice significantly; each control group (administered by an ingredient of the nutritional composition of the Example 1) has no significant influence on the immunity of the mice; the nutritional composition of the Example 1 has enhanced the immunity of the mice by comparison with the four control groups.

EXAMPLE 10

Anti-Oxidation Experiment on Composition 297 healthy male and female volunteers between 45 and 65 years of age were selected and randomly assigned into an experimental group, four control groups and a blank group. During the experiment, all the volunteers kept original living and dietary habits.

500 mg of the nutritional composition of the Example 2 were administered to the experimental group each time, two times a day for three consecutive months. 150 mg of selenium-enriched yeast (control group 1), 450 mg of yeast beta-glucan (control group 2), 2.5 mg of Vitamin C (control group 3) and 2.5 mg of Vitamin E (control group 4) were administered to the four control groups respectively each time, two times a day for three consecutive months. Subsequently, the content of lipid peroxide (malondialdehyde (MDA)), superoxide dismutase (SOD) activity and glutathione peroxidase (GSH-PX) activity of the volunteers were measured. The measurement method was the same as the method for evaluating health food.

From the experimental results, a conclusion can be drawn that the nutritional composition of the Example 2, on the one hand, can enhance the anti-oxidation capacity for human body and improve SOD activity and GSH-PX activity, and on the other hand, can decrease the MDA content in humans significantly. Each control group has no significant influence on the anti-oxidation capacity for human body. The nutritional composition of the Example 2 has enhanced the anti-oxidation capacity for human body by comparison with the four control groups.

| | | Blank group | Experimental group | Control group 1 |
|---|---|---|---|---|
| Volunteer quantity | | 50 | 51 | 45 |
| Age | | 51.3 ± 6.7 | 52.1 ± 7.3 | 50.1 ± 5.8 |
| Male/Female | | 25/25 | 28/23 | 25/20 |
| MDA content (nmol/mL) | Before administration | 5.74 ± 0.50 | 5.72 ± 0.55 | 5.69 ± 0.40 |
| | After administration | 5.66 ± 0.41 | 4.76 ± 0.60#* | 5.70 ± 0.65 |
| SOD activity (U/gHb) | Before administration | 13330.4 ± 2091.2 | 13205.8 ± 1267.6 | 13298.7 ± 1497.4 |
| | After administration | 13264.9 ± 1767.1 | 14350.9 ± 1429.2#* | 13378.1 ± 1783.6 |
| GSH-Px activity (U/mL) | Before administration | 121.9 ± 12.13 | 122.2 ± 11.77 | 120.4 ± 11.23 |
| | After administration | 120.1 ± 11.83 | 128.1 ± 11.20#* | 122.5 ± 15.44 |

| | | Control group 2 | Control group 3 | Control group 4 |
|---|---|---|---|---|
| Volunteer quantity | | 47 | 51 | 53 |
| Age | | 53.6 ± 8.1 | 49.4 ± 7.8 | 50.5 ± 6.2 |
| Male/Female | | 22/25 | 26/25 | 25/28 |
| MDA content (nmol/mL) | Before administration | 5.61 ± 0.51 | 5.77 ± 0.65 | 5.74 ± 0.55 |
| | After administration | 5.60 ± 0.34 | 5.75 ± 0.60 | 5.72 ± 0.65 |

-continued

| | | | | |
|---|---|---|---|---|
| SOD activity (U/gHb) | Before administration | 13278.5 ± 1879.4 | 13335.1 ± 1466.6 | 13297.0 ± 2193.7 |
| | After administration | 13287.3 ± 1997.7 | 13345.5 ± 1472.7 | 13375.6 ± 2014.7 |
| GSH-Px activity (U/mL) | Before administration | 117.5 ± 15.22 | 121.6 ± 15.67 | 120.8 ± 13.12 |
| | After administration | 118.8 ± 14.73 | 123.7 ± 15.33 | 121.9 ± 9.78 |

Remark:
Symbol "#" represents $p < 0.01$ by self-comparison;
symbol "*" represents $p < 0.01$ by comparison between groups.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A nutritional composition comprising by weight:
   between 0.05 and 30% selenium-enriched yeast;
   between 1 and 90% yeast beta-glucan;
   between 0.5 and 60% Vitamin C; and
   between 0.5 and 40% Vitamin E;
   wherein said composition has a synergistic effect on enhancing immunity and antioxidant capacity of a subject, and the synergistic effect is greater than a corresponding additive effect that selenium-enriched yeast, yeast beta-glucan, Vitamin C and Vitamin E would have when each is administered separately.

2. The composition of claim 1 comprising by weight:
   between 0.5 and 10% selenium-enriched yeast;
   between 20 and 58% yeast beta-glucan;
   between 20 and 40% Vitamin C; and
   between 20 and 30% Vitamin E.

3. The composition of claim 2, wherein said selenium-enriched yeast comprises between 500 and 2000 ppm of selenium.

4. The composition of claim 3, wherein said yeast beta-glucan comprises by weight between 20 and 90% of beta-glucan.

5. The composition of claim 4, further comprising by weight:
   between 0 and 1% Vitamin A;
   between 0- and 5% β-carotene;
   between 0 and 1% Vitamin $B_1$;
   between 0 and 1% Vitamin $B_2$;
   between 0 and 1% Vitamin $B_6$;
   between 0 and 5% lycopene;
   between 0 and 20% grape seed extract;
   between 0 and 20% α-lipoic acid;
   between 0 and 20% propolis;
   between 0 and 10% ginkgo biloba extract;
   between 0 and 10% ginseng extract;
   between 0 and 30% calcium carbonate;
   between 0 and 30% calcium gluconate;
   between 0 and 30% calcium lactate;
   between 0 and 10% zinc gluconate;
   between 0 and 10% zinc lactate;
   between 0 and 10% ferrous gluconate fumarate;
   between 0 and 1% ferrous lactate; and
   between 0 and 10% ferrous fumarate.

6. The composition of claim 1, wherein the composition comprises by weight:
   10% selenium-enriched yeast;
   30% yeast beta-glucan;
   40% Vitamin C; and
   20% Vitamin E.

7. The composition of claim 1, wherein the composition comprises by weight:
   30% selenium-enriched yeast;
   69% yeast beta-glucan;
   0.5% Vitamin C; and
   0.5% Vitamin E.

8. The composition of claim 1, wherein the composition comprises by weight:
   0.05% selenium-enriched yeast;
   90% yeast beta-glucan;
   3% Vitamin C; and
   6.95% Vitamin E.

9. The composition of claim 1, wherein the composition comprises by weight:
   5% selenium-enriched yeast;
   30% yeast beta-glucan;
   30% Vitamin C;
   20% Vitamin E; and
   15% sucrose.

10. The composition of claim 1, wherein the composition comprises by weight:
    10% selenium-enriched yeast;
    40% yeast beta-glucan;
    10% Vitamin C;
    10% Vitamin E,
    5% β-carotene;
    5% lycopene;
    5% propolis;
    5% starch; and
    10% sucrose.

11. The composition of claim 1, wherein the composition comprises by weight:
    17% selenium-enriched yeast;
    30% yeast beta-glucan;
    5% Vitamin C;
    5% Vitamin E,
    10% calcium carbonate;
    10% propolis;
    5% β-carotene;
    5% ginkgo biloba extract;
    5% grape seed extract;
    0.5% Vitamin $B_1$;
    0.5% Vitamin $B_2$;
    0.5% Vitamin $B_6$;
    1% ferrous lactate; and
    0.5% zinc gluconate.

12. The composition of claim 1, wherein the composition comprises by weight:
    0.5% selenium-enriched yeast;
    58% yeast beta-glucan;
    20% Vitamin C;
    4.5% Vitamin E,
    1% Vitamin A;
    5% α-lipoic acid;

4% ginseng extract;
2% calcium carbonate;
1% zinc lactate; and
4% ferrous gluconate.

13. The composition of claim 1, wherein the composition comprises by weight:
1% selenium-enriched yeast;
20% yeast beta-glucan;
15% Vitamin C;
30% Vitamin E;
0.5% Vitamin A;
1% Vitamin $B_1$;
1% Vitamin $B_2$;
1% Vitamin $B_6$;
20% grape seed extract;
2% calcium lactate;
2.5% ferrous fumarate; and
5% dextrin.

14. A composition comprising by weight:
between 0.05 and 30% selenium-enriched yeast;
between 1 and 90% yeast beta-glucan;
between 0.5 and 60% Vitamin C; and
between 0.5 and 40% Vitamin E;
wherein said composition has a synergistic effect on improving superoxide dismutase activity, antibody-producing capacity, and NK cell activity, and on decreasing lipid peroxide levels of a subject, and the synergistic effect is greater than a corresponding additive effect that selenium-enriched yeast, yeast beta-glucan, Vitamin C and Vitamin E would have when each is administered separately.

15. A method for improving superoxide dismutase (SOD) activity, glutathione peroxidase (GSH-PX) activity, or decreasing MDA levels in a patient, comprising administering to the patient the nutritional composition of claim 1.

16. A method for enhancing immunity, improving antibody-producing capacity, or improving NK cell activity in a patient, comprising administering to the patient the nutritional composition of claim 1.

* * * * *